(12) United States Patent
Gündel

(10) Patent No.: US 8,693,757 B2
(45) Date of Patent: Apr. 8, 2014

(54) METHOD AND DEVICE FOR THE AUTOMATIC CONTRAST MEDIUM PHASE CLASSIFICATION OF IMAGE DATA

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1478 days.

(21) Appl. No.: 12/320,247

(22) Filed: Jan. 22, 2009

(65) Prior Publication Data
US 2009/0190840 A1     Jul. 30, 2009

(30) Foreign Application Priority Data
Jan. 24, 2008  (DE) .......................... 10 2008 005 923

(51) Int. Cl.
*G06K 9/00* (2006.01)
(52) U.S. Cl.
USPC ............................ 382/131; 382/128; 382/132
(58) Field of Classification Search
None
See application file for complete search history.

(56) References Cited

U.S. PATENT DOCUMENTS

| | | | |
|---|---|---|---|
| 7,346,381 B2 * | 3/2008 | Okerlund et al. | 600/407 |
| 2004/0087850 A1 * | 5/2004 | Okerlund et al. | 600/407 |
| 2004/0250156 A1 * | 12/2004 | Weichselbaum | 714/2 |
| 2008/0212856 A1 * | 9/2008 | Oosawa et al. | 382/128 |
| 2009/0022375 A1 * | 1/2009 | Fidrich et al. | 382/128 |
| 2009/0090873 A1 * | 4/2009 | Sapp et al. | 250/459.1 |

* cited by examiner

*Primary Examiner* — Matthew Bella
*Assistant Examiner* — Jason Heidemann
(74) *Attorney, Agent, or Firm* — Harness, Dickey & Pierce, P.L.C.

(57) ABSTRACT

A method is disclosed for the automatic contrast medium phase classification of at least one image data record, of the interior of an examination object, generated by way of an imaging system. In at least one embodiment of the method, firstly at least one image data record of the examination object is acquired and metadata associated with the image data record are determined, the metadata including at least one of body region data containing information about a body region of the examination object that is covered by the image data record, and/or measurement time data containing information about a measurement time of the image data record and/or high contrast data containing information about highly contrasty image areas in the image data record. The assignment of the image data record to a contrast medium phase is effected, in at least one embodiment, in a manner dependent on the metadata. Furthermore, a description is given of a corresponding image data record classification device and an imaging system including such an image data record classification device.

24 Claims, 4 Drawing Sheets

METHOD AND DEVICE FOR THE AUTOMATIC CONTRAST MEDIUM PHASE CLASSIFICATION OF IMAGE DATA

PRIORITY STATEMENT

The present application hereby claims priority under 35 U.S.C. §119 on German patent application number DE 10 2008 005 923.4 filed Jan. 24, 2008, the entire contents of which is hereby incorporated herein by reference.

FIELD

At least one embodiment of the invention generally relates to a method for the automatic contrast medium phase classification of image data records of the interior of an examination object which are generated by way of an imaging system. Furthermore, at least one embodiment of the invention generally relates to an image data classification device which can be used for this purpose, and/or to an imaging system comprising such an image data record classification device, and/or to a computer program product by which the method according to at least one embodiment of the invention can be carried out.

BACKGROUND

Recordings of the interior of an examination object can be produced by way of various imaging systems that are able to represent the structures in the interior of the examination object. Computer tomography systems or magnetic resonance systems are typically used for this purpose. For easier identification of specific structures in the interior of an examination object, in many cases contrast media are used and image data records of the region of interest are produced during the spreading of the contrast medium in the examination object at different points in time.

By way of the contrast medium, which spreads, accumulates and dissipates again in or at specific structures in a particular manner, these structures become better distinguishable in the images and pathologies or dysfunctions become visible. In this case, the phase in which the images were recorded is significant, that is to say whether the phase is one in which the contrast medium first spreads into the structure or accumulates therein, or whether the images are generated in a phase in which the contrast medium slowly disappears again, that is to say is dissipated, from the structure. In order to be able to correctly assess the images later, it is important, therefore, to determine the contrast medium phase.

By way of example, in order to better identify tissue changes in human or animal bodies, in particular when searching for tumours or vascular diseases, e.g. embolisms, an intravenous contrast medium is usually injected. The latter passes via the right ventricle into the pulmonary circulation and from there via the left ventricle and the aorta or into the individual organs. If the image data records are generated at a point in time at which the contrast medium is flushed via the aorta or the further arteries into the organs, then this is referred to as the so-called "arterial phase".

Within an organ, the draining veins are then supplied via the capillary arteries, via which veins the contrast medium is washed out or dissipated again at a specific rate. This later point in time is defined as the "venous phase". In some organs a distinction can also be made between the normal "venous phase" and a "late venous phase". In the late venous phase, the residues of the contrast medium are flushed out.

For comparison purposes, an image data record without a contrast medium, that is to say generally prior to the contrast medium introduction, is generally also produced as well. This phase is referred to as the "native phase".

The control of imaging systems, in particular of large systems such as computer tomographs or magnetic resonance tomographs, is generally effected by way of so-called "scan protocols", which store all the essential machine parameters and also, in the case of recording sequences or studies, the time intervals between the individual recordings. In other words, the scan protocols contain the individual control parameters required for controlling the imaging system fully automatically in accordance with the scan protocol and for generating the desired image data records from the raw data acquired. In this case, different scan protocols are provided for a wide variety of recordings, that is to say that there are for example scan protocols for different body regions, for different recording methods and also—in the case of a contrast medium examination—for the successive recordings in the different contrast medium phases. In this case, a scan protocol may in particular also comprise a plurality of subprotocols constructed such that recordings in the different contrast medium phases are produced automatically.

The associated parameters can then be written to a header data area of the files containing the image data produced, in so far as the parameters are useful for the later evaluation. In the data standard DICOM (Digital Imaging and Communication in Medicine) used at the present time, the "DICOM files" each contain a "DICOM header" containing the parameters. In this case, the parameter "series description" generally also contains expressions such as "native", "arterial", "venous" or "late venous" which indicate the contrast medium phase.

These data originally accepted from the scan protocol can therefore be used, in principle. Unfortunately, however, this information is unreliable since the operators very often generate new scan protocols for new recordings by copying a scan protocol already present for other measurement tasks and then adapting the data of the scan protocol to the new measurement task. However, whether and in what form all of the entries are carefully adapted here is at the arbitrary discretion of the operator. This often has the consequence that in the scan protocols parameters which initially appear insignificant to the operator, such as the "series description", and which only describe the measurement but do not have an actual control effect are not adapted correctly. Errors can then occur in particular during a later evaluation of the image data using these additional data describing the contrast medium phase during the recording.

SUMMARY

In at least one embodiment of the present invention, a method is provided for the reliable automatic contrast medium phase classification of image data records and a corresponding image data record classification device.

The method according to an embodiment of the invention for the automatic contrast medium phase classification of image data records involves acquiring at least one image data record of the interior of the examination object which is to be classified. In addition, metadata associated with the image data record are acquired, these including body region data and/or measurement time data and/or contrast data. In this case, body region data should be understood to mean data containing information about a body region of the examination object which is covered by the image data record, e.g. the scan region covered and/or precise data about a specific target structure.

The measurement time data include data containing information about a measurement time of the image data record, that is to say for example the relative and/or absolute scan times at which the raw data for the respective image data were measured, but also data for determining the measurement times relative to the instant of a contrast medium introduction, that is to say the instants of the starting and stopping of a contrast medium pump. High contrast data should be understood to mean data containing information about highly contrasty image areas in the image data record, for example about structures that stand out to a high degree in the image on account of their intensities. According to an embodiment of the invention, the classification of the image data record is then effected by assigning the image data record to a contrast medium phase in a manner dependent on the metadata. In this case, preferably at least two of the metadata of abovementioned metadata types, that is to say body region data, measurement time data and/or high contrast data, are used for the classification. Particularly preferably, metadata of all three different metadata types are used in order to increase the reliability.

An image data record classification device according to an embodiment of the invention for the automatic contrast medium phase classification of image data records of the interior of an examination object which are generated by way of an imaging system has at least the following components:
a) An interface for acquiring at least one image data record of the examination object.
b) A metadata determining unit for determining metadata associated with the image data record which are of the following metadata types: body region data and/or measurement time data and/or high contrast data. This metadata determining unit can be, on the one hand, an interface which gathers the data from other apparatuses and devices or from existing data records, in particular specific metadata areas of the image data records, e.g. the DICOM headers. However, the metadata determining unit can also comprise components which analyze the data thus accepted and/or, if appropriate, also data obtained from the images themselves and generate further metadata therefrom.
c) An assigning unit for assigning the image data record to a contrast medium phase in a manner dependent on the metadata, that is to say for performing the actual classification.

Such an image data record classification device can be part of an imaging system. That is to say that the imaging system for generating image data records of the interior of an examination object, for example the computer tomography system or magnetic resonance system, can itself contain an image data classification device according to an embodiment of the invention. The device can be realized for example on a computer which is associated with the imaging system and on which the image data are reconstructed from the raw data.

In principle, however, a realization of such an image data record classification device can also be realized on other image processing systems which implement a network for example by way of the image data records from the imaging system. One example of this is traditional image computers in radiological information systems.

In this case, with a corresponding computer program product or computer readable medium in which the required interfaces, the metadata determining unit and the assigning unit are realized in the form of software components, it is also possible to upgrade or update an existing imaging system or image processing system in order to provide an image data record classification device according to an embodiment of the invention.

The dependent claims respectively contain particularly advantageous developments and configurations of embodiments of the invention, in which case the image data record classification device embodied according to an embodiment of the invention can also be developed in accordance with the method claims, and vice versa.

As already explained above, in the DICOM data format usually used at the present time, the files containing the image data record also contain a metadata area, the so-called DICOM header, which already contains metadata that were accepted during the creation of the files from the scan protocols.

Preferably, therefore, at least body region data and/or measurement time data can be accepted from such a metadata area of a number of files containing the image data record. The body region data can be for example the scan region defined in the scan protocol. Here it is possible e.g. to register whether a head examination, a thorax examination, liver examination, etc. is involved. The measurement time data can be absolute measurement time data that were automatically logged.

Preferably, the measurement time data can also be relative measurement times of the image data record in relation to the instant of a contrast medium introduction. However, these relative measurement time data can also be obtained from the absolute measurement times if the system logs precisely when a contrast medium pump was activated and shut down again. If the pump is driven by the imaging system, corresponding control data can also be accepted. The measurement time data can likewise comprise relative measurement times of different image data records of the examination object.

Since, as already mentioned, the image data record was usually generated on the basis of one or more scan protocols, at least some of the metadata can originate from the scan protocols. Other metadata, such as e.g. specific body region data and/or high contrast data, can preferably also be obtained from the image data record itself within an automatic image evaluation method. Thus, particularly contrasty structures in which a large amount of contrast medium has accumulated can be determined in a very simple manner by way of a threshold value method in the image data. Various methods for determining high contrast regions or specific structures having high contrasts are known in principle to the person skilled in the art.

Particularly preferably, the various metadata, if they are used for the assignment of the image data record to a contrast medium phase, are checked among one another for consistency in order thus to ensure an as reliable correct classification as possible.

Preferably, the individual metadata or metadata types are respectively assigned confidence values which are taken into account in the course of assigning the image data record to a contrast medium phase. In particular, such taking into account is expedient in the course of checking the various metadata among one another for consistency. These confidence values are assigned to the metadata particularly preferably in a manner dependent on the data source from which the relevant metadata originate. By way of example, all metadata which are automatically acquired by the system without the operator having any influence on this can be provided with a particularly high confidence value. In other words, these metadata are with very high probability correct. Metadata which, by contrast, can be altered by the operator and which can be gathered from the scan protocols, in particular, but which are not carefully adapted, if appropriate, during a modification of the scan protocols have only a low confidence value, by contrast.

The confidence values can be stored in a memory, for example, for the various metadata, or for the individual metadata types, and also for the various data sources.

If it is ascertained, for example, that different metadata exhibit an inconsistency with respect to one another, the metadata having a high confidence value are taken into account to a greater extent in the classification, whereas metadata having a low confidence value are taken into account only to a small extent or not at all. One example of this is the acceptance of body region data in the form of scan region data stored in the scan protocol, which have a relatively low confidence value since it is not certain whether the operator has incorrectly overwritten or not adapted the data. If these data are not consistent with structures which are determined from the image data records and which were obtained for example by determining high contrast regions, then it can be assumed with high probability that the body region data accepted from the scan protocol are incorrect. Such a case is present e.g. if an operator accepts a head scan protocol and adapts the latter in order to carry out an examination of a leg of the patient, but in the process forgets to change the description of the scan region (that is to say the parameter "series description" in the scan protocol) from "head" to "leg". In this case, incorrect body region data would automatically be accepted from the scan protocol, that is to say from the header of the DICOM file, the data indicating that a head examination is involved, whereas it was determined with the aid of the high contrast data that the examined region must indeed be a leg.

If the inconsistencies cannot be unambiguously eliminated on the basis of the confidence values and the analysis of further additional metadata, preferably a warning signal can also be output to the operator, with the result that the latter is made aware of the problem and he can resolve the inconsistency manually by corresponding data inputting.

As becomes clear from the example described above, determining the body region acquired can already be problematic. Therefore, the image data record classification device particularly preferably has a body region evaluation unit, which firstly on the basis of the body region data and/or the high contrast data automatically identifies the target structure imaged in an image data record, e.g. an organ to be examined or the aorta. Particularly preferably, the target structure is in this case localized directly in the image, that is to say that corresponding coordinates are determined. Consequently, the coordinates that are generally specified in the metadata area of the image files can simultaneously be checked and, if appropriate, corrected or a warning message can be output to an operator.

For determining or when processing the body region data, it is in particular also possible for different image data records of the examination object to be registered on one another. This is necessary for example when the image data records were recorded with a long time interval relative to one another and the patient was moved or settled again for example between two measurements. A typical case in this respect is recording in follow-up examinations which are intended to show a specific course. It is then generally necessary for recordings from the same contrast medium phases to be compared with one another. The registration of the different image data records on one another makes it possible firstly to ascertain whether the same body region is actually covered by the image data records.

Particularly significant parameters for determining the contrast medium phase are naturally the measurement time data, in particular relative measurement time data of the image data records with respect to one another and the relative measurement time data in relation to the contrast medium introduction. An identification of the contrast medium phase can thus already be effected jointly with the identified target structure. Preferably, therefore, the image data classification device has a measurement time evaluation unit, which identifies a possible contrast medium phase for an image data record on the basis of the identified target structure and the measurement time data.

Particularly preferably, the assigning unit is linked to the measurement time evaluation unit in such a way that the measurement time evaluation unit transfers to the assigning unit a contrast medium phase identifier representing the identified contrast medium phase for the image data record. The assigning unit then assigns the image data record to the relevant contrast medium phase if the assignment is consistent with high contrast data determined from the image data record. A two-stage check is effected, therefore, in the latter procedure. Firstly, a type of "candidate contrast medium phase" is determined in the measurement time evaluation unit. This result is then communicated to the assigning unit, which checks whether the identified contrast medium phase is actually consistent with the image data record. If so, the corresponding classification is effected.

BRIEF DESCRIPTION OF THE DRAWINGS

The invention is explained in more detail below on the basis of example embodiments with reference to the accompanying drawings, in which.

DETAILED DESCRIPTION OF THE EXAMPLE EMBODIMENTS

Figure 1:
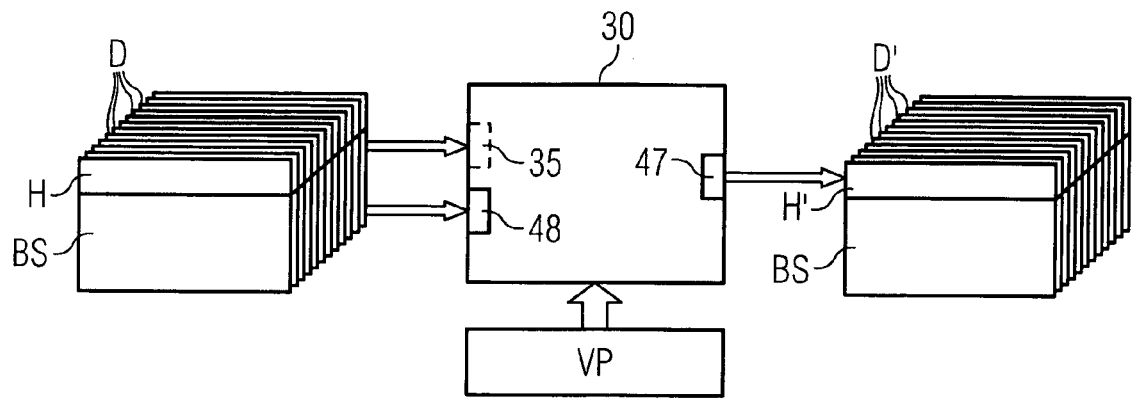
FIG. 1 shows a roughly schematic diagram of the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the example embodiments below it is assumed that the imaging system is a computer tomography system. It is furthermore assumed that, as usual at the present time, the image data records are created in the form of DICOM files by the imaging system and the DICOM header already contains metadata which were accepted from the scan protocol for the control of the computer tomography system. However, the invention is not restricted to the classification of image data records from computer tomography systems. Likewise, the embodiments of the invention is not restricted to the use of the DICOM standard.

As illustrated in FIG. 1, the image data records BS in the form of DICOM files D each having a DICOM header H are transferred to an image data classification device 30 according to an embodiment of the invention. The device has an interface 48 for accepting the image data records BS and also a metadata determining unit 35, which here is illustrated in the form of a separate interface 35 which accepts the metadata from the header H of the files D. Alongside corresponding interface components, which can also be part of the interface 48, the metadata determining unit 35 also has further components, however, for determining metadata in a different way. This will be explained in more detail below with reference to FIG. 2.

Moreover, the image data record classification device 30 additionally receives confidence parameters VP assigned to the different metadata. The confidence parameters VP describe how reliable the information contained in the respective metadata is. From these data, the image data record classification device then determines with a high probability the contrast medium phase in which the present image data record BS was recorded, and enters the contrast medium phase determined in the form of a description, an identifier or any other data string which represents the contrast medium phase into the DICOM header H of the files D with the corresponding image data record BS. In particular, it is possible to appropriately enter or overwrite the parameter "series description" in the DICOM header or a corresponding indication in a metadata part of the files.

The result is then modified files D' which in turn contain the input image data records BS but a modified DICOM header H' in which the correct contrast medium phase has been entered with high reliability. Image data postprocessing programs which wish to access specific image data records comprising contrast medium phases can then evaluate this information. One example of this is an image postprocessing program set up for automatically finding lesions (so-called "computer aided detection"=CAD). In such image postprocessing devices, modified algorithms for processing the image data records are provided for each contrast medium phase.

The image data classification device 30 is explained in more detail below with reference to FIG. 2. The image data record classification device 30 illustrated in FIG. 2 additionally has, alongside the actual assigning unit 31, a measurement time evaluation unit 32 and a body region evaluation unit 33, the function of which will be explained in more detail below. These components can in particular also be combined in an assigning unit 31.

The metadata determining unit 35 of the image data record classification device 30 in this case comprises a multiplicity of individual components 36, 37, 38, 39, 40, 41, 42, 43, 44, 45, 46. These components, 36, . . . , 46, just like the assigning unit 31, the measurement time evaluation unit 32 and the body region evaluation unit 33, can be constructed in the form of software modules. In this case, the individual components 36, . . . , 46 of the metadata determining unit 35 can be simple software interfaces which for example in each case accept specific metadata, metadata already generated from the header of the DICOM files D by other components. However, the components can also be components which either determine or extract the respective metadata from the image data or process accepted metadata further and generate further metadata therefrom.

As already explained, one essential point is the precise definition of the body region acquired or of the organ acquired. There are various metadata for determining the body region. First, the scan protocol writes the body region into the so-called "series description" of the DICOM header H in the course of creating the image data records. This parameter is accepted for example by a reading unit 39. In this case, in a logic unit 46 firstly an interrogation is made as to whether the "series description" in the DICOM header H of the image data series actually contains a body region. If so, these are transferred as first body region data $KBD_1$ to the body region evaluation unit 33. Alongside the body region, the contrast medium phase can also be input directly in this "series description" by the scan protocol. However, since the scan protocols in practice are often used for a different application than the originally planned application, the values $KBD_1$ are in each case provided with a very low confidence parameter and generally have to be checked against further body region data $KBD_2$, $KBD_3$, $KBD_4$ for consistency.

Alongside the "series description", in the DICOM header there is also a further DICOM entry (also called "DICOM tag" hereinafter), which directly describes the body region, such as, for example, "abdomen", "pelvis", "chest", "neck", "head", etc. These DICOM tags of the image data records are also accepted from the scan protocol and are accordingly to be provided with a low confidence value. These data are read out from the header H by way of a reading unit 40 and transferred as further body region data $KBD_2$ to the body region evaluation unit 33, which in turn checks them for consistency with the first body region data $KBD_1$.

A further component 41 is an image evaluation unit 41, which automatically detects the body region. Suitable algorithms for identifying specific structures in computer tomography data with high reliability already exist. An allocation of the body region acquired is thereby possible with high trustworthiness, such that the body region data $KBD_3$ acquired by the image evaluation unit 41 can be provided with a high confidence value. Bones such as e.g. skull, ribs, hip bones and the bones of the extremities are of particular interest here. Data records comprising a plurality of body regions can also be identified.

The header of the DICOM files also usually contains so-called "DICOM coordinates", which describe the coordinates of the image in a defined standard. These coordinates refer to a virtual zero point, the so-called "frame of reference", of the patient coordinate system. The "frame of reference" is a data string on the basis of which it is possible to determine whether the position of the patient on the scanner of the computer tomography system has changed between two recordings. At least within a study carried out without moving the patient, a fixed "frame of reference" can be taken as a basis. The DICOM coordinates then correspond to the patient coordinates to a first approximation. The "frame of reference" in the DICOM header can be acquired by a reading unit 43, and the DICOM coordinates defined thereon can be acquired by the reading unit 42. These data are firstly transferred to a scan region checking unit 44.

In aftercare examinations in which for example the course of a disease is intended to be clarified, the same contrast medium phases have to be compared with one another. If the position of the initial examination is known, for example in the form of DICOM coordinates, the position of the follow-up examination can also be derived therefrom. This also functions if the scan regions and patient positions of the image data records to be compared are different.

In order to establish whether two image data records cover the same body region, they must firstly be registered on one another. This is effected in a registration unit 45, which supplies the result likewise to the scan region checking unit 44. A registration is illustrated schematically in FIG. 3. A first image data record BS1, covering the scan region $SB_1$, was acquired during an initial examination. An image data record $BS_2$, covering a wider scan region $SB_2$, is recorded in a follow-up examination. Moreover, the patient has shifted by comparison with the initial examination in the computer tomography apparatus. With the aid of the registration REG, the two image data records are registered on one another in order thus to determine a common reference. If the reference is known, then it is subsequently possible to work with the DICOM coordinates.

The DICOM coordinates thus determined, which, if appropriate, are adjusted by a registration for different image data records on one another, are then transferred as further body region data $KBD_4$ to the body region evaluation unit 33.

It is pointed out at this juncture that the different reading units described individually here for reading out data from the DICOM header H can also be realized by a common interface which reads out all the data all at once and distributes them to the corresponding components for further processing. An illustration of individual components was chosen in FIG. 2 merely for the sake of clarity.

Finally, the body region evaluation unit 33 checks all the body region data $KBD_1$, $KBD_2$, $KBD_3$, $KBD_4$ for consistency, taking account of the confidence parameters, and then decides which body regions are represented by the image data record or which organs are imaged.

For further support, the body region evaluation unit 33 can also accept high contrast data HKD from a high contrast detector unit 38. The introduction of contrast medium leads to very high CT values in the arterial phase in the main arteries, which values can easily be detected in the images. If the body region is roughly known, then it is possible to search for particularly significant structures in the relevant body region. By way of example, it is possible to search for the aorta in a targeted manner in the abdomen. Conversely, the body region can be deduced on the basis of the vessel size and position, the trustworthiness decreasing with the diameter of the vessel examined. In this respect, the high contrast data can be assigned a confidence value in a manner dependent on the detected structure, for example the artery diameter when detecting arteries. In this case, it is also possible to take account of the fact that the contrast medium pervasion can be reduced by a partial occlusion of a vessel in such a way that high computer tomography values can be identified only with very great difficulty in the image.

A further component is a scan time determining unit 36, which reads out measurement time data TMZ from the header H of the DICOM files D of the image data record BS. During the scan, the current date and time of day are usually entered in the DICOM header H. Since the system does this independently, the trustworthiness is high and the corresponding measurement time data TMZ containing the absolute measurement times, that is to say the times at which the raw data were acquired, with date and time of day, are provided with a high confidence value.

By way of a contrast medium time determining unit 37, start and end instants of the contrast medium introduction are determined as further measurement time data TKG and transferred to the measurement time evaluation unit 32. The confidence parameter with which the data are provided depends on how the measurement time data TKG were determined. If the times of the contrast medium pump are transmitted via a fixed coupling to the computer tomography system or if the computer tomography system is even driven by the contrast medium pump or, conversely, the contrast medium pump is controlled by the computer tomography system, then the measurement time data concerning the contrast medium introduction are highly trustworthy and are accordingly provided with a high confidence parameter. If manual inputting is provided, then lower confidence parameters have to be fixed.

If the precise start point and the end point of the contrast medium introduction are known, the contrast medium phase can be deduced directly by the measurement time evaluation unit from the absolute scan times TMZ and the back-calculation thereof relative to the start and end points of the contrast medium introduction and also the body region or the target structure identified precisely by the body region evaluation unit 33.

Furthermore, indications about the contrast medium phase can be obtained from the relative measurement times of the different image data records. Image data records of the same body region from a study (that is to say a series of associated image data records during the contrast medium examination) are usually always in the order "native", "arterial", "venous" and "late venous", though not always all the phases have to be present. The interval between the native scan and the scans with contrast medium can be as long as desired, in principle. This is rarely the case, however, in practical operation. Likewise, the native scan could theoretically also be recorded after the contrast medium scans, but this is likewise highly unusual in practice. The intervals between the individual scans with the contrast medium introduction depend on the distribution of the contrast medium in the body.

An example that may be mentioned for the liver is for example 10 to 20 sec for the arterial phase and 40 to 75 sec for the late venous phase. Different body regions can also be examined with a contrast medium introduction; e.g. firstly the arterial phase of the lung and subsequently in the same scan the arterial phase of the liver. From the relative data, too, it is therefore possible for contrast medium phases to be automatically detected in conjunction with information about the body region.

Figure 2:
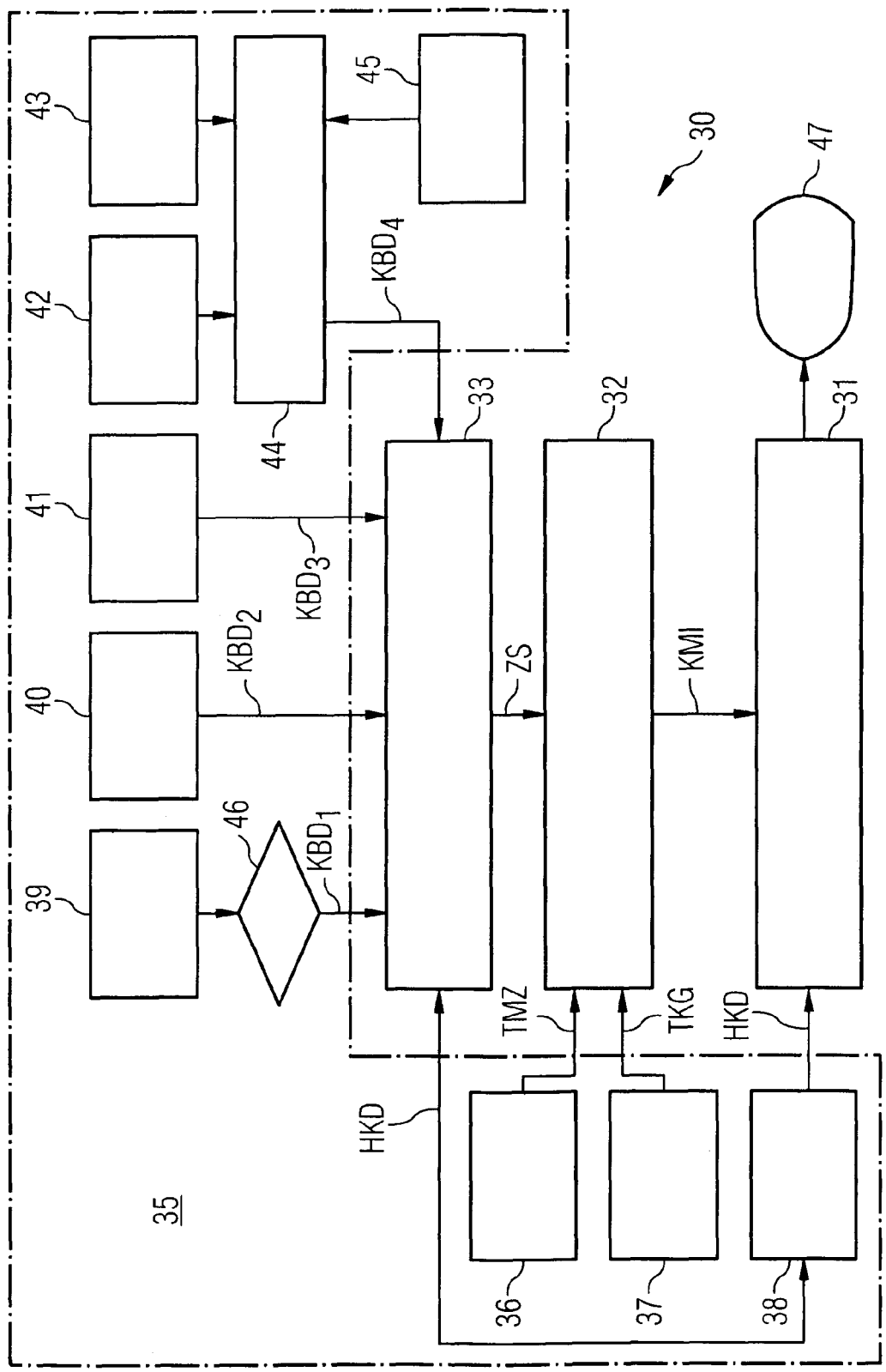
FIG. 2 shows a schematic block diagram of an image data record classification device according to an embodiment of the invention.

The functioning of the image data classification device described in FIG. 2 is as follows:

In most cases, it is necessary firstly to determine the body region of at least one image data record. For this purpose, the DICOM tags "series description" and "body part examined" are read out from the DICOM header by the reading units 39, 40 and are evaluated as body region data $KBD_1$, $KBD_2$ jointly with body region data $KBD_3$ detected automatically by the image evaluation unit 41. The reliability of the different parameters is taken into account in this case.

In the scan region checking unit 44, the scan region of a plurality of image data records is compared with one another. If the scan region is identical, then it is possible to derive directly from the DICOM coordinates read out by the reading unit 42 whether they are associated with the same body region. If it is found in the scan region checking unit 44 that the "frame of reference" of the different image data records read in by way of the reading unit 43 is different, then the DICOM coordinates are not directly comparable. In this case, with the aid of the registration unit 45, firstly the image data records are registered on one another in order thus to create a common reference.

Figure 3:
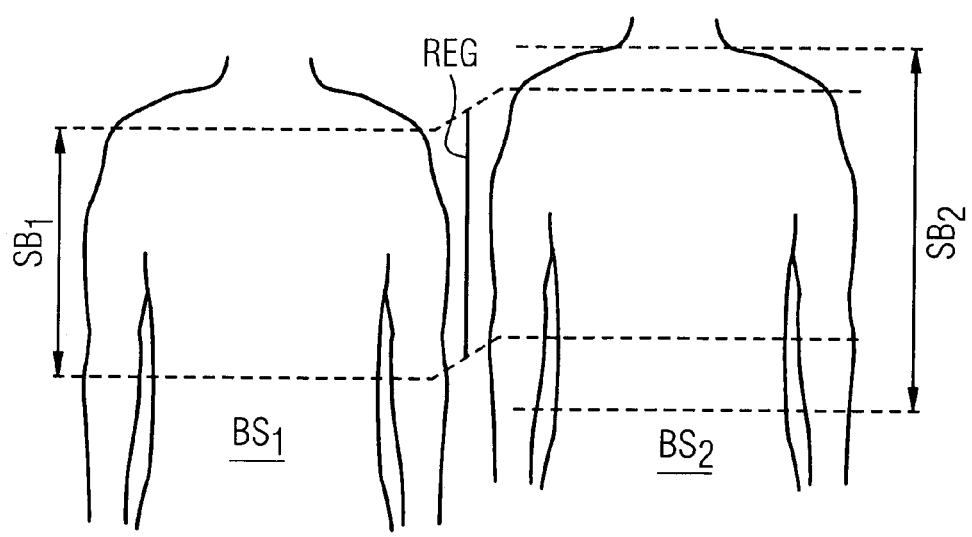
FIG. 3 shows a schematic illustration of a registration of two image data records on one another.

In the scan region checking unit 44 a decision is also made as to whether an image data record is lengthened, that is to say whether, as illustrated schematically on the right-hand side of FIG. 3, an adjacent body region is concomitantly acquired. It is thus entirely possible, for example, to acquire the thorax and the abdomen in the native scan and for example to examine only the thorax during the subsequent contrast medium measurement in the arterial scan.

As already explained, regions having high CT values can be detected in a particularly simple manner in the CT images, e.g. by threshold value methods. This is effected in the high contrast detection unit 38. The high contrast data determined in this case can likewise be made available to the body region evaluation unit 33.

If the body region acquired has already been successfully detected, then the aorta enhanced with contrast medium is sought in a targeted manner for example in the chest region and in the abdomen with the aid of the high contrast data. The allocation to the "arterial phase" is thereby made possible. However, if the body region is not yet known or is known only with low reliability, for example on account of inconsistencies, then the body region can be inferred on the basis of the position and number of the high contrast vessels and the scan region can thus be verified even better.

As soon as a target structure ZS, for example a specific body region and/or a specific organ, has been unambiguously determined, it can be transferred to the measurement time evaluation unit 32, where the time differences in the data records and also the relative time at the start and end of the contrast medium introduction are used for classification. It is initially assumed here that image data records having time differences below a specific time difference threshold of a few minutes are associated with an examination.

Figure 4:
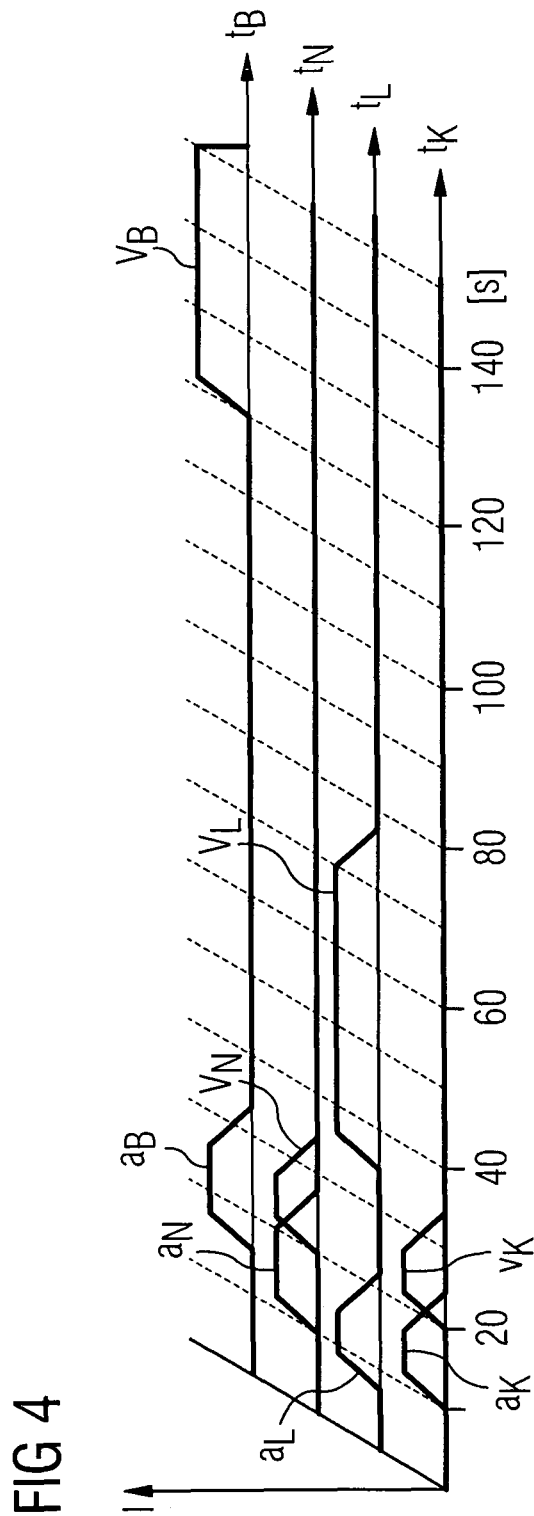
FIG. 4 shows a simple graphical illustration of the temporal profile of the arterial and venous contrast medium pervasion in different body regions.

FIG. 4 shows typical times of arterial and venous contrast medium pervasion for a selection of organs and body regions. Such values can also be defined for other organs and body regions. In this case, the contrast medium intensity I in the computer tomography images for different organs and body parts is plotted respectively on different time lines $t_K$, $t_L$, $t_N$, $t_B$ lying one behind another. $t_K$ is the time line for the head, $t_L$ is the time line for the liver, $t_N$ for the kidneys and $t_B$ for the legs.

FIG. 4 here shows the intensity increase in each case only roughly schematically. The first intensity increases respectively show the arterial phase $a_K$, $a_L$, $a_N$, $a_B$, the second increases respectively show the venous phase $v_K$, $v_L$, $v_N$, $v_B$, the venous phase $v_B$ for the legs also being referred to as the late venous phase.

FIG. 4 shows clearly that for the legs and the liver the differences are readily separable using a crisp logic, e.g. by way of a threshold value. For the head region and the kidneys, by contrast, the pervasion regions $a_K$, $v_K$, $a_N$, $v_N$ overlap in such a way that a fuzzy logic can advantageously be used here. The use of a fuzzy decision unit is appropriate for this purpose in the evaluation, in which case the values shown in FIG. 4 can also be used directly for the so-called fuzzification of the measurement time evaluation unit 32.

For the case where the absolute instant of the contrast medium introduction is known and trustworthy, it is also possible in accordance with FIG. 4 to work with the absolute numerical values, that is to say with the relative times for the contrast medium introduction. Otherwise only the time differences in the individual scans, that is to say in the individual image data records, with respect to one another are to be taken into account.

With the aid of the measurement times and the body region determined, in most cases the contrast medium phase can already be determined without any problems. In FIG. 2 this is effected directly in the measurement time evaluation unit 32, which then communicates a "candidate contrast medium phase indicator" KMI to the assigning unit 31, or a corresponding value or a data string representing the selected contrast medium phase. The assigning unit 31 then checks the "candidate contrast medium phase" obtained with the high contrast data for consistency and, by way of the writing device 47, then writes the contrast medium phase determined or a value representative thereof or a data string to the header H of the file D containing the image data record.

It goes without saying that it is also possible for the target structure ZS to be transferred directly to the assigning unit 31 by the body region evaluation unit and for the measurement time evaluation unit merely to evaluate the relative and absolute measurement times and also to transfer these to the assigning unit 31, such that ultimately solely the contrast medium phase is determined there.

One example of determining the contrast medium phase is given on the basis of the table below. It is assumed here that the "frame of reference" is identical for all the image data records and that the "series description" and the parameter "body part examined" in the DICOM header respectively reads "thorax", "abdomen". In other words, no rational statement is possible.

| SN | HKD | ZS | Δt | DICOM coordinates in Z direction | Assignment |
|---|---|---|---|---|---|
| 1 | Negative | Thorax Abdomen | — | 100 . . . 600 mm | 2: "native phase" |
| 2 | Positive | Thorax Abdomen | 3 min | 100 . . . 600 mm | 1: "arterial phase" |
| 3 | Negative | Abdomen | 10 s | 350 . . . 600 mm | 4: "venous phase" of the kidney |
| 4 | Negative | Abdomen | 25 s | 300 . . . 500 mm | 5: "venous phase" of the liver |
| 5 | Negative | Abdomen | 3 min | 300 . . . 500 mm | 3: "late venous phase" |

In this case, the first column of the table contains a scan number SN, that is to say the number of the image data record. The second column indicates whether a specific structure, here the aorta, could respectively be identified in the high contrast data HKD (positive=aorta was found, negative=aorta could not be identified). The third column contains the target structures ZS identified in the image data record, here the body region. The fourth column contains the time difference Δt with respect to the previous scan and with respect to the previously recorded image data record. The fifth column contains the DICOM coordinates in the z direction, and the sixth column contains the assignment made.

The first assignment that could be made very easily was the assignment of scan No. 2. Here the arterial phase was detected since the high contrast detection found the aorta. Consequently, the image data record from scan 2 is unambiguously associated with the "arterial phase".

The image data record of scan 1 was then assigned in the second step. Since the DICOM coordinates of scan 1 and scan 2 are identical and scan 1 temporally precedes scan 2, the "native phase" is involved here.

Thirdly, the late venous phase was then assigned to scan 5. This scan 5 has a significantly larger time interval with respect to scan 4 and the late venous phase is thus involved, with high probability the liver since such scans are customary only in that case.

The venous phase of the kidney is subsequently assigned to scan 3 in step 4. In accordance with FIG. 4, the time difference Δt of scan 3 suggests the venous phase of head or kidney. However, the DICOM coordinates rule out the head. On account of the time difference of scan 4 with respect to the arterial phase of 35 sec, a venous scan of the liver is unambiguously involved.

This example shows how the recorded image data records can be automatically and reliably assigned to a contrast medium phase. Consequently, automatic evaluations of the image data records which rely on the correct information about the contrast medium phase can also subsequently be made with corresponding reliability.

Figure 5:
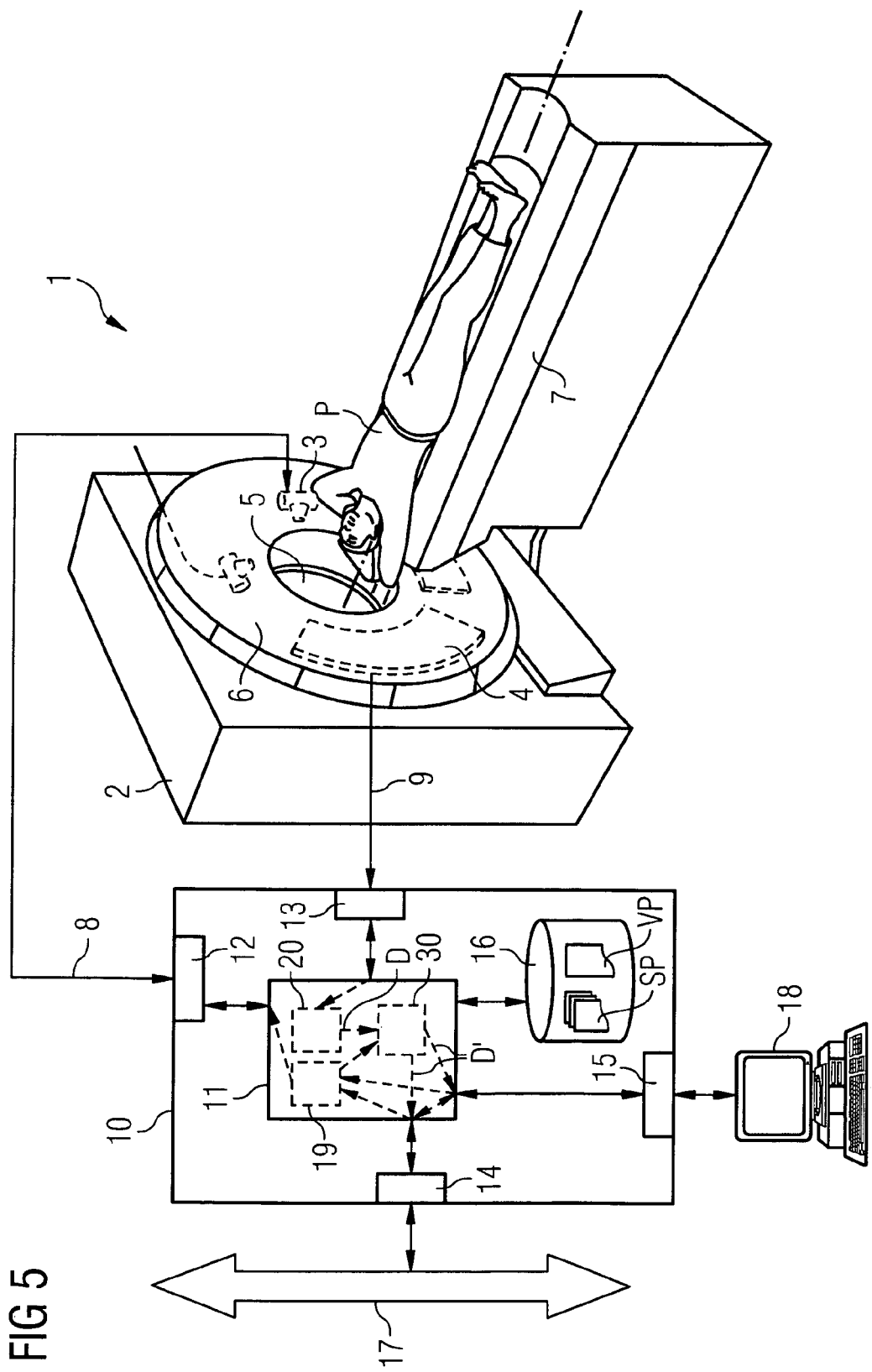
FIG. 5 shows a schematic illustration of an example embodiment of a computer tomography system with an integrated image data record classification device.

Finally, FIG. 5 shows an example embodiment of a computer tomography system 1 for carrying out the method according to an embodiment of the invention. An essential constitute part here is the scanner 2, which has a gantry housing 6 with an x-ray source 3 circulating around a measurement space 5 and a generally likewise circulating x-ray detector 4 situated opposite the x-ray source 3 in each case.

For measurement purposes, the patient P is placed onto a patient's couch 7 in a customary manner, the couch being mounted in movable fashion on a base part such that the patient P can be moved through the measurement space 5.

It is expressly pointed out that this is only an example embodiment and embodiments of the invention can, of course, also be used in systems in which the gantry moves along the patient and the patient lies on the couch at a fixed position. Other types of detectors can likewise be used, for example detectors which extend along the entire circumference and which do not move concomitantly, rather in which only the x-ray tube 5 rotates. Variants with a plurality of x-ray tubes 5 or other constructions are furthermore possible.

The gantry with its components is controlled by way of a control device 10 having a processor 11, a plurality of interfaces 12, 13, 14, 15, and a memory 16. A terminal 18 for operating the computer tomography system 1 is connected via a first interface 15. A further interface 14 serves for connection to a network 17, for example an RIS network (RIS=radiological information system) and/or a PACS network (PACS=picture archiving and communication system). Via this network 17, image data and/or raw data can be communicated to mass storage devices, output units, findings stations, workstations or the like.

Via a control interface 12, a signal can be communicated via a control line 8 to the x-ray tube 5 in order to appropriately drive the latter. The gantry can also be controlled by this device. For the sake of simplicity, a common control interface 12 and only one control line 8 are shown only schematically for all control tasks.

In order to generate the respective recordings in the desired manner, a driving unit 19 realized in the form of software is also situated on the processor 11. The driving unit 19 accepts specific scan protocols SP from the memory 16, for example, for driving the scanner 2 for a specific measurement. A control device 10 for a computer tomography system usually contains a multiplicity of such scan protocols SP for a wide variety of examination situations in a memory 16, in which case the operator can respectively select, and possibly modify, an appropriate scan protocol SP via the terminal 30. After the start of the measurement, the entire computer tomography system 1 then operates in accordance with the control parameters in the selected scan protocol.

Via a raw data acquisition interface 13, the raw data are acquired at the appropriate points in time from the detector 4 via a data line 9. The measured raw data are communicated to an image reconstruction unit 20, which creates the image data records therefrom and writes them to the DICOM files D.

The DICOM files D are then transferred to the image data record classification device 30 according to an embodiment of the invention, which operates as described above and modifies the DICOM files D' to the effect that the automatically determined contrast medium phase assigned to the respective image data record is written in the header H'. For this purpose, the image data classification device 30 can access the values in the headers H of the original DICOM files D and additionally use confidence parameters VP likewise stored in the memory 16. The confidence parameters VP can also be altered by the operator via the terminal 18.

The completed DICOM files D' can then for example be output via the interface 15 to the operator's terminal 18 or be sent via the interface 14 and network 17 to other components such as viewing stations, archiving stations or printers, etc.

The image reconstruction unit 20 and the image data record classification device 30 are realized here in the form of software on the processor 11. In principle, however, the image reconstruction unit 20 and the image data record classification device 30 can also be realized on some other computer which is connected to the network 17 and to which the raw data are firstly communicated via the network 17. Shifting all or part of the image processing to an external workstation has the advantage that the burden on the control device 10 is relieved and the control device 10 is therefore available more rapidly for further measurements.

It is clear that a computer tomography system 1 used for embodiments of the invention can furthermore also additionally have a multiplicity of further customary components which, however, are not illustrated further in FIG. 5 for reasons of simplification and need not actually be explained in any further detail since they are known to the person skilled in the art.

Finally, it is pointed out once again that the method and system architecture described in detail above are merely example embodiments which can be modified in diverse ways by the person skilled in the art without departing from the scope of the invention in so far as this scope is prescribed by the claims. For the sake of completeness, it is also pointed out that the use of the indefinite article "a" or "an" does not preclude the fact that the relevant features can also be present multiply. Likewise, the term "unit" does not preclude the fact that the latter comprises a plurality of components which, if appropriate, can also be distributed spatially.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic contrast medium phase classification of at least one image data record, of an interior of an examination object, generated by way of an imaging system, the method comprising:
    acquiring the at least one image data record of the examination object;
    determining metadata associated with the acquired at least one image data record, the metadata including at least one of,
        body region data containing information about a body region of the examination object that is covered by the at least one image data record,
        measurement time data containing information about a measurement time of the at least one image data record, and
        high contrast data containing information about highly contrasty image areas in the at least one image data record;
    assigning confidence values to the determined metadata; and
    assigning the at least one image data record to a contrast medium phase in a manner dependent on the determined metadata and the assigned confidence values.

2. The method as claimed in claim 1, further comprising: checking the metadata among one another for consistency.

3. The method as claimed in claim 1, wherein the assigning confidence values is based on a data source from which the metadata originates.

4. The method as claimed in claim 1, wherein the measurement time data includes a relative measurement time of the at least one image data record in relation to the instant of a contrast medium introduction.

5. The method as claimed in claim 1, wherein the at least one image data record includes a plurality of image data records and wherein the measurement time data includes relative measurement times of different image data records of the examination object with respect to one another.

6. The method as claimed in claim 1, further comprising:
    accepting at least one of body region data and measurement time data from a metadata area of a number of files containing the at least one image data record.

7. The method as claimed in claim 1, further comprising:
    accepting at least one of body region data and high contrast data from the at least one image data record.

8. The method as claimed in claim 1, wherein the at least one image data record is generated on a basis of a number of scan protocols and the method further comprises accepting at least some of the metadata from the scan protocols.

9. The method as claimed in claim 1, wherein the at least one image data record includes a plurality of image data records and the method further comprises, for determining the body region data, registering different image data records of the examination object on one another.

10. The method of claim 1, wherein the method for automatic contrast medium phase classification of image data records is performed by an image data record classification device, wherein the acquiring occurs via an acquiring unit of the image data record classification device, wherein the determining occurs via a metadata determining unit of the image data record classification device and wherein the assigning occurs via an assigning unit of the image data record classification device.

11. The method of claim 1, wherein the determined metadata includes at least two of the body region data, the measurement time data, and the high contrast data.

12. A non-transitory computer program product, loadable directly into a memory of an image processing system, comprising a tangible computer readable medium including program code segments embedded thereon for executing the method as claimed in claim 1 upon the program product being executed on the image processing system.

13. A non-transitory computer readable medium including program segments embedded thereon for, when executed in an image processing system, causing the image processing system to implement the method of claim 1.

14. A memory of an image processing system, comprising program code segments for executing the method as claimed in claim 1.

15. An image data record classification device for automatic contrast medium phase classification of at least one image data record, of an interior of an examination object, generated by way of an imaging system, the image data record classification device comprising:
   an interface configured to acquire the at least one image data record of the examination object; and
   at least one processor configured to,
      determine metadata associated with the at least one image data record, the metadata including at least one of,
         body region data containing information about a body region of the examination object that is covered by the at least one image data record,
         measurement time data containing information about a measurement time of the at least one image data record, and
         high contrast data containing information about highly contrasty image areas in the at least one image data record,
      assign confidence values to the determined metadata, and
      assign the at least one image data record to a contrast medium phase in a manner dependent on the determined metadata and the assigned confidence values.

16. The image data record classification device as claimed in claim 15, further comprising:
   a body region evaluation unit configured to, on the basis of at least one of the body region data and the high contrast data, automatically identify a target structure imaged in the at least one image data record.

17. The image data record classification device as claimed in claim 16, further comprising:
   a measurement time evaluation unit configured to, on the basis of the identified target structure and the measurement time data, identify a possible contrast medium phase for the at least one image data record.

18. The image data record classification device as claimed in claim 17, wherein the assigning unit is linked to the measurement time evaluation unit such that the measurement time evaluation unit is configured to transfer to the assigning unit a contrast medium phase identifier representing the identified contrast medium phase for the at least one image data record, and the assigning unit is configured to assign the at least one image data record to the relevant contrast medium phase if the assignment is consistent with high contrast data determined from the at least one image data record.

19. The device of claim 15, wherein the determined metadata includes at least two of the body region data, the measurement time data, and the high contrast data.

20. An imaging system for generating at least one image data record of the interior of the examination object, comprising the image data record classification device as claimed in claim 15.

21. An image data record classification device for automatic contrast medium phase classification of at least one image data record, of an interior of an examination object, generated by way of an imaging system, the image data record classification device comprising:
   means for acquiring the at least one image data record of the examination object;
   means for determining metadata associated with the acquired at least one image data record, the metadata including at least one of,
      body region data containing information about a body region of the examination object that is covered by the at least one image data record,
      measurement time data containing information about a measurement time of the at least one image data record, and
      high contrast data containing information about highly contrasty image areas in the at least one image data record;
   means for assigning confidence values to the determined metadata; and
   means for assigning the at least one image data record to a contrast medium phase in a manner dependent on the determined metadata and the assigned confidence values.

22. The device of claim 21, wherein the determined metadata includes at least two of the body region data, the measurement time data, and the high contrast data.

23. An imaging system for generating at least one image data record of the interior of the examination object, comprising the image data record classification device as claimed in claim 21.

24. An image data record classification device for automatic contrast medium phase classification of at least one image data record, of an interior of an examination object, generated by way of an imaging system, comprising:
   an interface configured to acquire the at least one image data record of the examination object;
   at least one processor configured to,
      determine metadata associated with the at least one image data record, the metadata including at least one of,
         body region data containing information about a body region of the examination object that is covered by the at least one image data record,
         measurement time data containing information about a measurement time of the at least one image data record, and high contrast data containing information about highly contrasty image areas in the at least one image data record, and assign the at least one image data record to a contrast medium phase in a manner dependent on the determined metadata;

a body region evaluation unit configured to, on the basis of at least one of the body region data and the high contrast data, automatically identify a target structure imaged in the at least one image data record; and a measurement time evaluation unit configured to, on the basis of the identified target structure and the measurement time data, identify a possible contrast medium phase for the at least one image data record, wherein the assigning unit is linked to the measurement time evaluation unit such that the measurement time evaluation unit is configured to transfer to the assigning unit a contrast medium phase identifier representing the identified contrast medium phase for the at least one image data record, and the assigning unit is configured to assign the at least one image data record to the relevant contrast medium phase if the assignment is consistent with high contrast data determined from the at least one image data record.

* * * * *